(12) United States Patent
Fioramonti et al.

(10) Patent No.: US 7,294,337 B2
(45) Date of Patent: Nov. 13, 2007

(54) **USE OF *LACTOBACILLUS FARCIMINIS* FOR THE PREVENTION OR TREATMENT OF DIGESTIVE PATHOLOGIES**

(75) Inventors: Jean Fioramonti, Roquettes (FR); Lionel Bueno, Aussonne (FR); Vassilia Theodorou, Portet-sur-Garonne (FR); Florence Lamine, Toulouse (FR)

(73) Assignee: Institut National de la Recherche Agronomique (INRA), Paris (FR)

( * ) Notice: Subject to any disclaimer, the term of this patent is extended or adjusted under 35 U.S.C. 154(b) by 0 days.

(21) Appl. No.: 10/509,255

(22) PCT Filed: Mar. 21, 2003

(86) PCT No.: PCT/FR03/00903

§ 371 (c)(1),
(2), (4) Date: May 23, 2005

(87) PCT Pub. No.: WO03/082307

PCT Pub. Date: Oct. 9, 2003

(65) Prior Publication Data

US 2005/0244389 A1    Nov. 3, 2005

(30) Foreign Application Priority Data

Mar. 28, 2002  (FR) .................... 02 03891

(51) Int. Cl.
*A61K 39/00*  (2006.01)
*A61K 45/00*  (2006.01)
*A01N 63/00*  (2006.01)

(52) U.S. Cl. ............... 424/184.1; 424/93.1; 424/93.45; 424/282.1

(58) Field of Classification Search ............. 424/184.1, 424/93.4, 96.46, 93.42, 252.1, 93.1, 93.45, 424/282.1
See application file for complete search history.

(56) References Cited

U.S. PATENT DOCUMENTS

2005/0153018 A1 * 7/2005 Ubbink et al. ................ 426/61
2005/0232909 A1 * 10/2005 Farmer .................... 424/93.45

FOREIGN PATENT DOCUMENTS

FR    WO 98/27991    *  7/1998

OTHER PUBLICATIONS

WebMDHealth (http://mywebmed.com/hw/inflammatory_bowel/uf6012.asp).*
(http://www.HealingWithNutrition.com/idisease/inflambowel/chrohns.html).*
InteliHealth (http://www.intelihealth.com).*
Venturi et al (Impact on the composition of faecal flora by a new probiotic preparation: preliminary data on maintenance treatment of patients with ulcerative colitis, Aliment Pharmacol Ther, 1999; 13: 1103-1108).*
Nobaek et al (Alteration of intestinal microflora is associated with reduction in abdominal bloating and pain in patients with irritable bowel syndrome, The American Journal of Gastroenterology, 2000; 95(5): 1231-1238).

* cited by examiner

*Primary Examiner*—Robert A. Zeman
*Assistant Examiner*—Lakia J Tongue
(74) *Attorney, Agent, or Firm*—Morgan Lewis & Bockius (57) ABSTRACT

The invention relates to the use of lactic bacteria of the species *Lactobacillus farciminis* for the treatment or prevention of a pathology of the digestive tube, especially an acute or chronic inflammatory pathology of the intestine.

3 Claims, 8 Drawing Sheets

USE OF *LACTOBACILLUS FARCIMINIS* FOR THE PREVENTION OR TREATMENT OF DIGESTIVE PATHOLOGIES

CROSS REFERENCE TO RELATED APPLICATION

This is a National Stage application filed under 35 U.S.C. § 371 of PCT/FR03/00903 filed Mar. 21, 2003, which claims priority to France Application No. 02/03891 filed Mar. 28, 2002, all of which are herein incorporated by reference.

The present invention relates to the use of the lactic acid bacterium *Lactobacillus farciminis* for the prevention or treatment of digestive, in particular functional and/or inflammatory, pathologies.

Numerous pathologies of the digestive tube, and in particular of the intestine, involve to a greater or lesser degree inflammatory phenomena. Among these pathologies, there may be mentioned in particular:

intestinal chronic inflammatory diseases, which include mainly Crohn's disease and hemorrhagic rectocolitis, constitute a pathology of low prevalence, but which is however on the increase. These diseases, which are highly incapacitating, are characterized by inflammatory attacks of variable seriousness with sometimes prolonged phases of remission. The current therapy is mainly based on the administration of corticoids, of 5-ASA (5-aminosalicylic acid), surgery in the most serious cases. Treatments with certain cytokines have been proposed, but they are still at the experimental stage, and remain expensive;

functional digestive disorders (FDD), which constitute a pathology with low morbidity but of very high prevalence. Visceral pain is the main symptom, but other digestive symptoms (diarrhea, constipation or alternation of the two) or extradigestive symptoms (fatigue) are often associated. Its physiopathology remains imprecise (impairments of the gastrointestinal motility, involvements of psychosocial factors, after-effects of digestive inflammation and of surgery), but painful hypersensitivity to distension of the digestive wall is a principal characteristic of this pathology. The origin of this hypersensitivity is not known, although an inflammatory origin has been assumed because of the prolongation of FDDs for several months in a high proportion of patients suffering from an acute gastroenteritis, and by the demonstration of inflammatory after-effects (hyperplasia of the mastocytes) in digestive mucous membranes of patients with FDD.

Various teams have reported the efficacy of probiotic microorganisms in the context of the treatment of these pathologies of the digestive tube. The name "probiotic" groups together live microorganisms of various families, genera and species, which, when they are ingested in a sufficient quantity, exert a positive effect on health, extending beyond the traditional nutritional effects.

Studies showing the efficacy of probiotics in the treatment of experimental digestive inflammations have thus been carried out with *Lactobacillus reuteri* (FABIA et al., Scand. J. Gastroenterol., 28, 155-162, 1993; HOLMA et al., Scand. J. Gastroenterol., 36, 630-635, 2001) and *Lactobacillus plantarum* (MAO et al., Gastroenterology, 111, 334-344, 1996). Recently, a study in humans has shown the efficacy of *Saccharomyces boulardii* in the prevention of the recurrence of Crohn's disease (GUSLANDI et al., Dig. Dis. Sci., 45, 1462-1464, 2000). Other probiotics have also shown efficacy in the treatment of hemorrhagic rectocolitis: *Escherichia coli* Nissle (KRUIS et al., Aliment. Pharmacol. Ther., 11, 853-858, 1997); REMBACKEN et al., Lancet, 354, 635-639, 1999), a combination of strains of *Bifidobacterium, Lactobacillus* and *Streptococcus* (VENTURI et al., Aliment. Pharmacol. Ther., 13, 1103-1108, 1999) and a combination *Bifidobacterium bifidum, Bidobacterium breve, Lactobacillus acidophilus* (ISHIKAWA et al., Gastroenterology, 118, 4171, 2000).

As regards functional digestive disorders, and irritable bowel syndrome, the results are less convincing: one study showed that *Saccharomyces boulardii* reduced diarrhea associated with functional digestive disorders but did not affect the other symptoms (MAUPAS et al., Med. Chir. Dig., 12, 77-79, 1983) and another study reports the inefficacy of a combination of strains of *Lactobacillus* and of *Escherichia coli* in the treatment of nonulcerative dyspepsia (HENTSCHEL et al., Gastroenterology, 112 Suppl 1, A146, 1997); positive effects of *Lactobacillus plantarum* on several symptoms of irritable bowel syndrome (flatulence, abdominal pain) have been observed, but these effects are similar to those of a placebo for the abdominal pain criterion (NOBAEK et al., Am. J. Gastroenterol., 95, 1231-1238, 2000); another study relating to three of the symptoms of irritable bowel syndrome (pain, "fecal incontinence", distensions) reports the absence of an effect of *Lactobacillus casei* CG (O'SULLIVAN et al., Dig. Liver Dis., 32, 294-301, 2000).

It therefore appears that the use of probiotic microorganisms for the treatment of inflammatory pathologies of the digestive tube constitutes a promising approach, but whose efficacy appears variable, both according to the species of microorganism used and according to the pathology or pathological symptom in question. It is therefore desirable to identify other microorganisms which can be used for this purpose in order to broaden the range of therapeutic possibilities.

The inventors have now discovered that lactic acid bacteria of the genus *farcinimis* of the species *Lactobacillus* were active in vivo on the inflammation of the digestive tube, and in particular of the colon, and on visceral pain. The inventors observed that the antiinflammatory activity of *Lactobacillus farcinimis* was due to the production in situ in the digestive lumen of nitric oxide (NO) by this bacterium. *Lactobacillus faciminis* belongs to group I (strict homofermenter) of the species *Lactobacillus*. It is frequently found in various food products such as meat products, in particular sausages, and Baker's yeast (DE ROISSARD and LUQUET, Bactéries lactiques, Volume I: Aspects fondamentaux et technologiques, Lorica, 1998). The production of nitric oxide in culture by *Lactobacillus farciminis* has been reported by WOLF et al., Int. J. Food Microbiol., 10, 323-329, 1990. A potential role of nitric oxide in the regulation of the digestive functions and/or the protection of the digestive mucous membrane has been suggested by various observations. It is known that some cells of the intestinal epithelium can produce nitric oxide after induction by certain proinflammatory cytokines and/or by the lipopolysaccharide toxins (LPS) of enteroinvasive bacteria (WITTHOFT et al., Am. J. Physiol., 275, G564-571, 1998). This endogenous nitric oxide is thought to participate, through its antimicrobial properties, in the defence against pathogenic microorganisms. It is also thought to participate, when it is produced in low quantities, in protecting the intestinal mucous membrane. However, in larger quantities, it is thought to contribute to the onset and maintenance of a chronic inflammatory state (ALICAN and KUBES, Am. J.

Physiol. 270, G225-237, 1996; TEPPERMAN et al., J. Pharmacol. Exp. Ther., 271, 1477-1482, 1994).

As regards exogenous nitric oxide (that is to say resulting from the diet or from a drug administration), the effects observed are also contradictory; a transient protective effect of NO donors in relation to ethanol induced lesions in the gastric mucous membrane has been observed (MAC NAUGHTON et al., Life Sci., 45, 1869-1876, 1989), as well as a protective effect in relation to lesions induced by hydrochloric acid (KITAGAWA et al., J. Pharmacol. Exp. Ther., 253, 1133-1137, 1990). Other studies have shown that the local intraarterial infusion of NO donors can cause variable effects in relation to hemorrhagic impairment of the gastric mucous membrane: a protective effect, an absence of effect or a deleterious effect may be observed depending on the nature of the NO donor and the dose used (LOPEZ-BELMONTE et al., Br. J. Pharmacol., 108, 73-78, 1993).

A few probiotic microorganisms are currently known whose effects appear to be due, at least in part, to an influence on the production of endogenous NO. PCT application WO 00/28943 shows that some strains of lactic acid bacteria, and in particular of *Lactobacillus casei*, can have an antiinflammatory action by increasing the production of nitric oxide by the enterocytes activated by proinflammatory cytokines, and by decreasing, in contrast, the production of nitric oxide by the enterocytes activated by proinflammatory cytokines and bacterial lipopolysaccharides. KORHONEN et al. (Inflammation, 25, 223-232, 2001) have shown that the GG strain of *Lactobacillus rhamnosus*, which is active on viral or antibiotic-induced diarrheas, can increase the production of nitric oxide by intestinal epithelial cells or macrophages activated by proinflammatory cytokines, and indicates that this effect on the production of NO could be involved in the activity of *Lactobacillus rhamnosus*.

The possible probiotic effects of microorganisms which are directly producers of nitric oxide have only been studied to a very limited extent. PCT application WO 98/27991 proposes the use of bacteria of the genus *Propionobacter*, which are producers of nitric oxide, for the production of a composition producing physiologically significant quantities of NO in the digestive tube, and reports an effect of this composition on intestinal motility. This document also mentions *Lactobacillus farciminis*, but to exclude the use thereof, on the basis of experimental trials in culture from which it is concluded that the quantity of NO produced by *L. farciminis* is too low to be significant.

In contrast to what was indicated in PCT application WO 98/27991, the inventors have now established that *L. farciminis* produces, in the digestive tube, a quantity of nitric oxide allowing it to exert a therapeutic effect, in particular an antiinflammatory effect and an effect on pain related to visceral distension.

The subject of the present invention is the use of a lactic acid bacterium of the species *Lactobacillus farciminis* for the production of a composition intended for the treatment or prevention of pathologies of the digestive tube.

The *L. farciminis* type strain which was used in the context of the experiments which led to the present invention is known per se and accessible in various collections; it is for example referenced under the following accession numbers: CIP-103136T, ATCC 29644, DSM 20184, JCM 1097, LMG 9200, NCDO 2330, NCIB 11717, IMET 11462. It is also possible to use, for carrying out the present invention, strains of *L. farciminis* isolated from food products containing this bacterium. According to a preferred embodiment of the present invention, said composition is intended for the treatment of acute or chronic inflammatory pathologies of the digestive tube, and in particular of the intestine.

According to another preferred embodiment of the present invention, said composition is intended for the treatment or prevention of visceral pain.

By way of examples of pathologies for the treatment of which the present invention may be used, there may be mentioned colitis, enteritis, Crohn's disease, hemorrhagic rectocolitis, functional digestive disorders (irritable bowel syndrome and nonulcerative dyspepsia) and the like.

Preferably, said composition is intended for oral administration.

It may comprise one or more strains of *L. farciminis*, in any formulation which makes it possible to keep these bacteria viable during the various stages of their packaging and their storage, and after their ingestion, up to their site of action in the digestive tube.

It may also optionally comprise other lactic acid bacteria, possessing or not possessing probiotic properties, for example with bacteria such as lactobacilli, lactococci, streptococci and bifidobacteria, and/or other probiotic microorganisms such as yeasts.

In the context of the present invention, the compositions comprising *L. farciminis* may be administered in the form of foods. This may be for example fermented products such as dairy products; in this case, *L. farciminis* may be part of the ferment used for the production of these products, or alternatively may be added to them after fermentation. They may also be administered in the form of dietary supplements to be incorporated into the diet, or to be ingested directly. Advantageously, they may be packaged in the form of individual doses containing the desired quantity of *L. farciminis*.

To carry out the present invention, *L. farciminis* would be preferably administered in an amount of at least $10^6$ CFU (colony forming units)/day, advantageously at least $10^8$ CFU/day, and most preferably at least $10^{10}$ CFU/day, as single or divided doses.

The present invention will be understood more clearly with the aid of the additional description which follows, which refers to nonlimiting examples illustrating the properties of a *Lactobacillus farciminis* strain in relation to a colonic inflammation and from visceral pain to distension.

EXAMPLE 1

Effect of a Treatment with *Lactobacillus Farciminis* on a Colonic Inflammation Induce by TNBS/Ethanol: Role of Nitric Oxide (NO)

A colonic inflammation (or colitis) may be experimentally induced by trinitrobenzenesulfonic acid (TNBS), which constitutes the most common and best validated model of experimental colonic inflammation (MORRIS et al., Gastroenterology, 96, 795-803, 1989).

This colitis is characterized by an increase in myeloperoxidase (MPO) activity, a marker of the degree of infiltration of polynuclear neutrophils in the colonic mucosa, and by the increase in the macroscopic lesion score (MLS) taking into account the seriousness and the extent of the macroscopic lesions appearing, the presence and seriousness of adherences and the presence or nonpresence of diarrhea in the colon.

The effects of a treatment with a nitric oxide donor, sodium nitroprusside (SNP), or with *L. farciminis* on a TNBS-induced colitis in rats were compared. Moreover, the effective role of exogenous nitric oxide in these effects was evaluated using an NO scavenger, hemoglobin (Hb).

For the study of the effects of SNP, 7 groups of WISTAR rats of 200-250 grams were provided, under anesthetic, with an intracolonic catheter (+2 cm from the caeco-colonic junction) exteriorized at the level of the dorsoscapular region. At D+5, the rats receive an intracolonic instillation of 80 mg/kg/day of TNBS/ethanol (groups 4-7) or of a 0.9% NaCl solution (groups 1-3). 4 hours after the instillation, the rats are infused at a flow rate of 250 μl/hour with 1 mg/kg/day of SNP (groups 2 and 5), or 200 mg/kg/day of Hb (groups 3 and 7), or an SNP+Hb mixture (group 6), or a 0.9% NaCl solution (groups 1 and 4), for 4 days.

For the study of the effects of *L. farciminis*, 5 groups of 10 male WISTAR rats of 200-250 grams receive orally $10^{12}$ CFU/day of *L. farciminis* (groups 2, 4, 5) or a 0.9% NaCl solution (groups 1, 3), for 19 days. At D+10, the rats are provided with an intracolonic catheter as described above. At D+15, the rats receive by the intracolonic route 80 mg/kg of TNBS/ethanol (groups 3-5) or a 0.9% NaCl solution (groups 1, 2). 4 hours after the instillation, the rats receive an intracolonic infusion of Hb, at 200 mg/kg/day (group 5) or of a 0.9% NaCl solution (groups 1-4), for 4 days.

At D+19, all the rats are sacrificed and the severity of the inflammation of the colon wall is characterized by the myeloperoxidase (MPO) activity and the macroscopic lesion score (MLS), on colon samples isolated.

I—Myeloperoxidase (MPO) Activity

The myeloperoxidase (MPO) activity is determined on colon samples isolated according to the protocol described by BRADLEY et al. (J. Invest. Dermatol., 78, 206-209, 1982).

This protocol may be summarized as follows:

The colon segments (1 cm long) are immersed in phosphate buffer (50 mM, pH 6). After mechanical lysis on ice with the aid of a POLYTRON homogenizer, 3 freezing (liquid nitrogen, 1 min) and thawing (waterbath, 37° C., 10 min) cycles are performed. After centrifugation (10 000 rpm, 15 min, 4° C.), the pellet is taken up in 0.5% hexadecyltrimethylammonium bromide (HTAB). The samples are then sonicated before being subjected to another centrifugation. The supernatant is recovered for assays of MPO activity and of total proteins.

The MPO activity is determined by spectrophotometry. The sample is brought into contact with phosphate buffer containing O-dianisidine dihydrochloride (0.167 mg/ml) and 0.0005% hydrogen peroxide. The changes in absorbance (450 nm, 25° C.) were determined by kinetic spectrophotometry of 2 minutes, according to the balanced equation for the enzymatic reaction catalyzed by MPO: $H_2O_2 + Cl^- = H_2O + HOCl$ (orange color), and expressed as MPO units.

One MPO activity unit is defined as the quantity of MPO degrading 1 μmol of hydrogen peroxide per minute per milliliter at 25° C. The protein concentration (grams/ml) is determined with the aid of a commercial kit (Detergent Compatible Assay, Bio Rad, Ivry/Seine, France). The MPO activity is expressed in the form of MPO units per gram of proteins (MPO U/g of proteins).

1) Treatment with SNP

Figure 1:
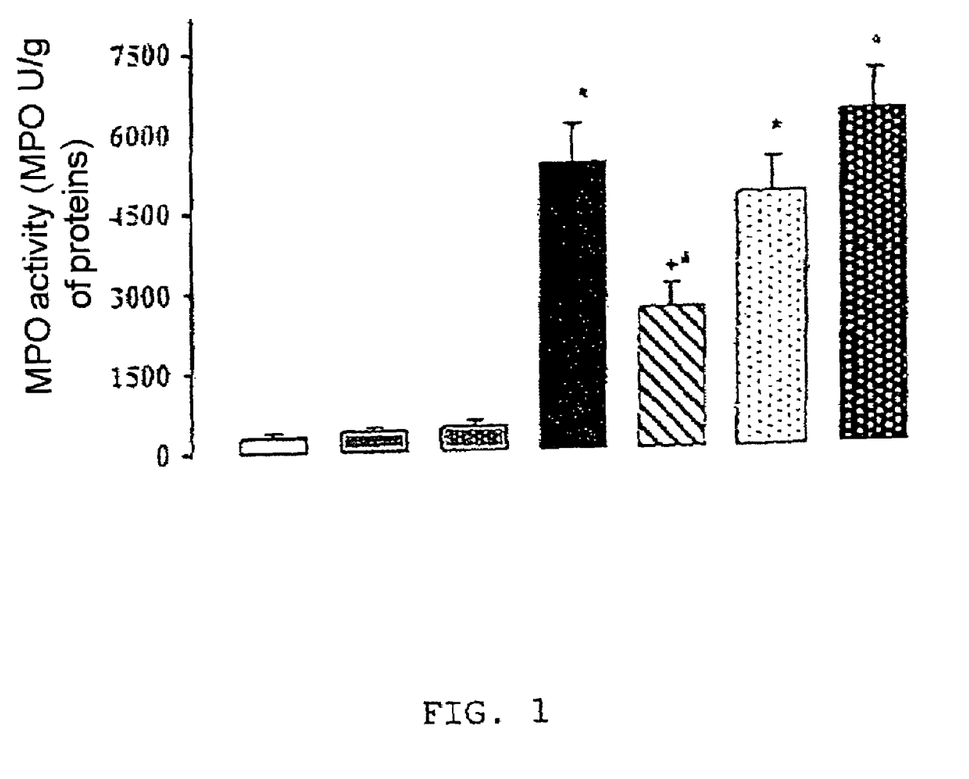
FIG. 1 shows myeloperoxidase (MPO) activity (MPO U/g of protein) in rats after treatment with SNP.

The results are presented in FIG. 1.

Legend to FIG. 1:

On the x-axis

□=untreated rats (group 1)

▨=rats treated with SNP (group 2)

▩=rats treated with Hb (group 3)

■=rats treated with TNBS/ethanol (group 4)

▨=rats treated with TNBS/ethanol+SNP (group 5)

▨=rats treated with TNBS/ethanol+SNP+Hb (group 6)

▨=rats treated with TNBS/ethanol+Hb (group 7)

On the y-axis=MPO activity (MPO U/g of proteins)

\*: significantly different (P<0.01) from the control group (group 1)

+: significantly different (P<0.01) from the TNBS/ethanol group (group 4)

The MPO activity of the colon wall in the control rats (group 1) and those treated with SNP (group 2) or Hb (group 3), in the absence of instillation of TNBS/ethanol, is 263±103; 351±88; 426±117 MPO U/g of proteins, respectively. These values are not significantly different from each other. The instillation of TNBS/ethanol (group 4) significantly increases the MPO activity compared with the control rats (5346±712 MPO U/g of proteins). The infusion of SNP into the rats instilled with TNBS/ethanol (group 5) significantly reduces the MPO activity (2619±447 MPO U/g of proteins) compared with the rats which only received an instillation of TNBS/ethanol. The combined infusion of SNP and Hb into the rats instilled with TNBS/ethanol (group 6) abolishes the reduction of the MPO activity induced by SNP (4710±645 MPO U/g of proteins), no significant difference appearing compared with the rats instilled with TNBS/ethanol (group 4; 5346±714 MPO U/g of proteins).

2) Treatment with *L. farciminis*

Figure 2:
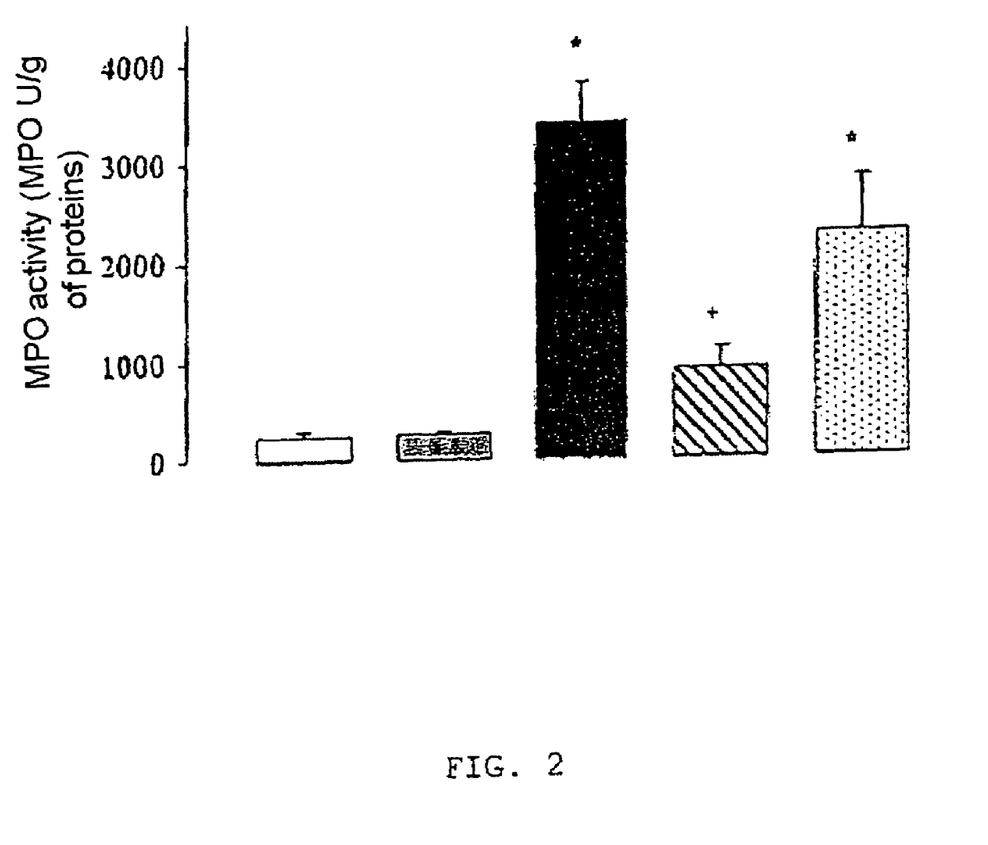
FIG. 2 shows MPG activity (MPG U/g of protein) in rats after treatment with *L. farciminis*.

The results are illustrated by FIG. 2.

Legend to FIG. 2:

On the x-axis

□=untreated rats (group 1)

▨=rats treated with *L. farciminis* (group 2)

■=rats treated with TNBS/ethanol (group 3)

▨=rats treated with *L. farciminis*+TNBS/ethanol (group 4)

▨=rats treated with *L. farciminis*+TNBS/ethanol+Hb (group 5)

On the y-axis=MPO activity (MPO U/g of proteins)
*: significantly different (P<0.01) from the control group (group 1)
+: significantly different (P<0.01) from the TNBS/ethanol group (group 3)

The untreated control rats (group 1) have an MPO activity of 273±53 MPO U/g of proteins.

The instillation of TNBS/ethanol induces a colonic inflammation characterized by an increase in the MPO activity (group 3; 3400±395 MPO U/g of proteins). The treatment with *L. farciminis* has no effect on the MPO activity in the rats instilled with the salt solution (group 2; 256±31 MPO U/g of proteins). By contrast, in the rats instilled with TNBS/ethanol, the treatment with *L. farciminis* significantly reduces the MPO activity (group 4; 905±211 MPO U/g of proteins). The infusion of hemoglobin abolishes the reduction in the inflammation caused by *L. farciminis* in the rats instilled with TNBS/ethanol (group 5; 2246±566 MPO U/g of proteins).

II—Macroscopic Lesion Score (MLS)

The macroscopic lesion score (MLS) is determined on isolated colonic samples as described by WALLACE et al., (Gastroenterology, 102, 18-27, 1992) according to the assessment grid below:

| Parameter | Score |
| --- | --- |
| Ulceration | |
| Normal appearance | 0 |
| Focal hyperemia without ulceration | 1 |
| Ulceration without hyperemia or thickening of the mucous membrane | 2 |
| Ulceration at 1 inflammatory site | 3 |
| Ulceration at 2 or more inflammatory sites | 4 |
| Several inflammatory sites over more than 1 cm | 5 |
| Inflammatory surface area >2 cm, score increased by 1 for each ulcerated cm | 6-10 |
| Adhesion | |
| No adherence | 0 |
| Slight adherence | 1 |
| Strong adherence | 2 |
| Diarrhea | |
| No | 0 |
| Yes | 1 |
| Total score | |

1) Treatment with SNP

Figure 3:
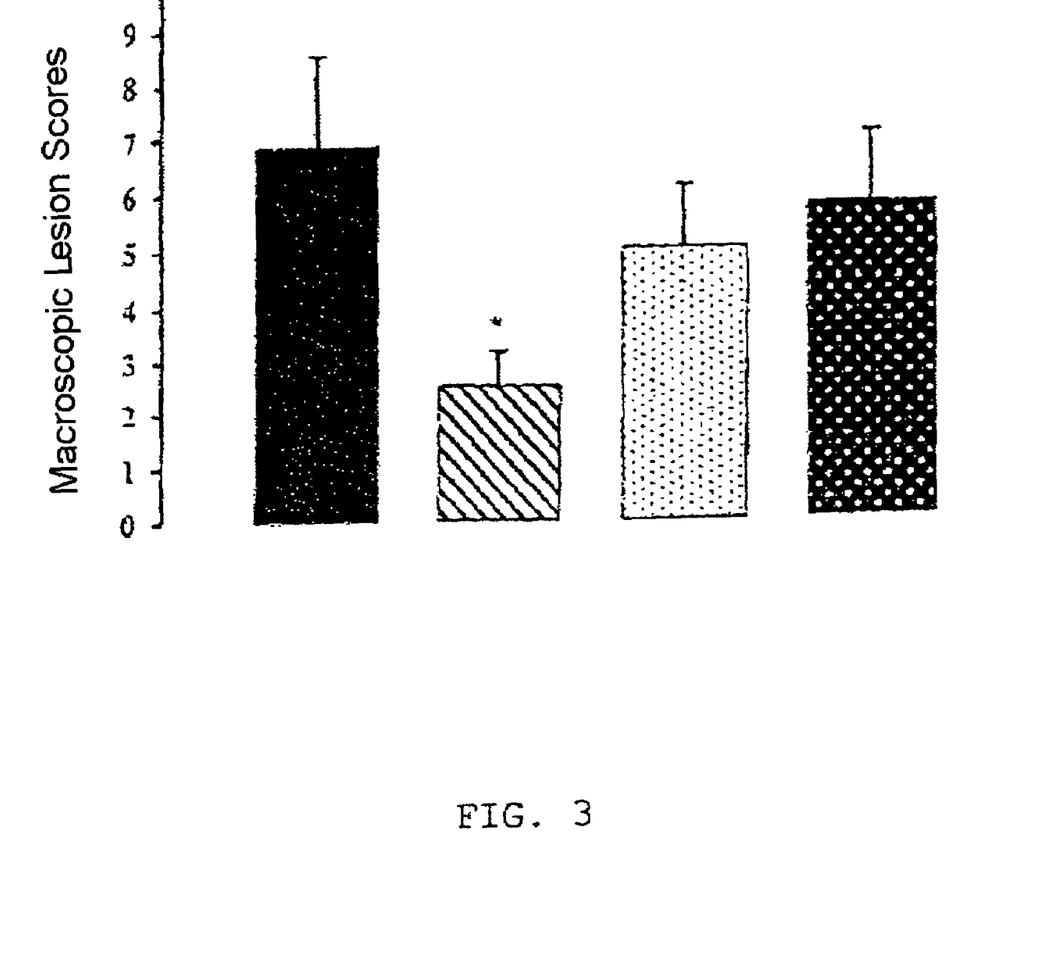
FIG. 3 shows macroscopic lesion scores in rats after treatment with SNP.

The results are illustrated by FIG. 3.
Legend to FIG. 3:
On the x-axis
■=rats treated with TNBS/ethanol (group 4)
☒=rats treated with TNBS/ethanol+SNP (group 5)
▨=rats treated with TNBS/ethanol+SNP+Hb (group 6)
▦=rats treated with TNBS/ethanol+Hb (group 7)
On the y-axis=macroscopic lesion scores
*: significantly different (P<0.01) from the control group (groups 1-3)

4 days after the instillation of TNBS/ethanol, the colonic mucosa is characterized by a substantial ulceration associated with a regular inflammation and a wall thickness corresponding to an MLS of 6.9±1.7 (group 4). The daily treatment with SNP significantly reduces the extent of the colonic lesion, reducing the MLS to 2.5±0.6 (group 5), whereas the daily treatment with SNP+Hb and Hb alone has no effect on this parameter with respective MLSs of 5.0±1.1 (group 6) and 5.8±1.3 (group 7).

2) Treatment with *Lactobacillus farciminis*

Figure 4:
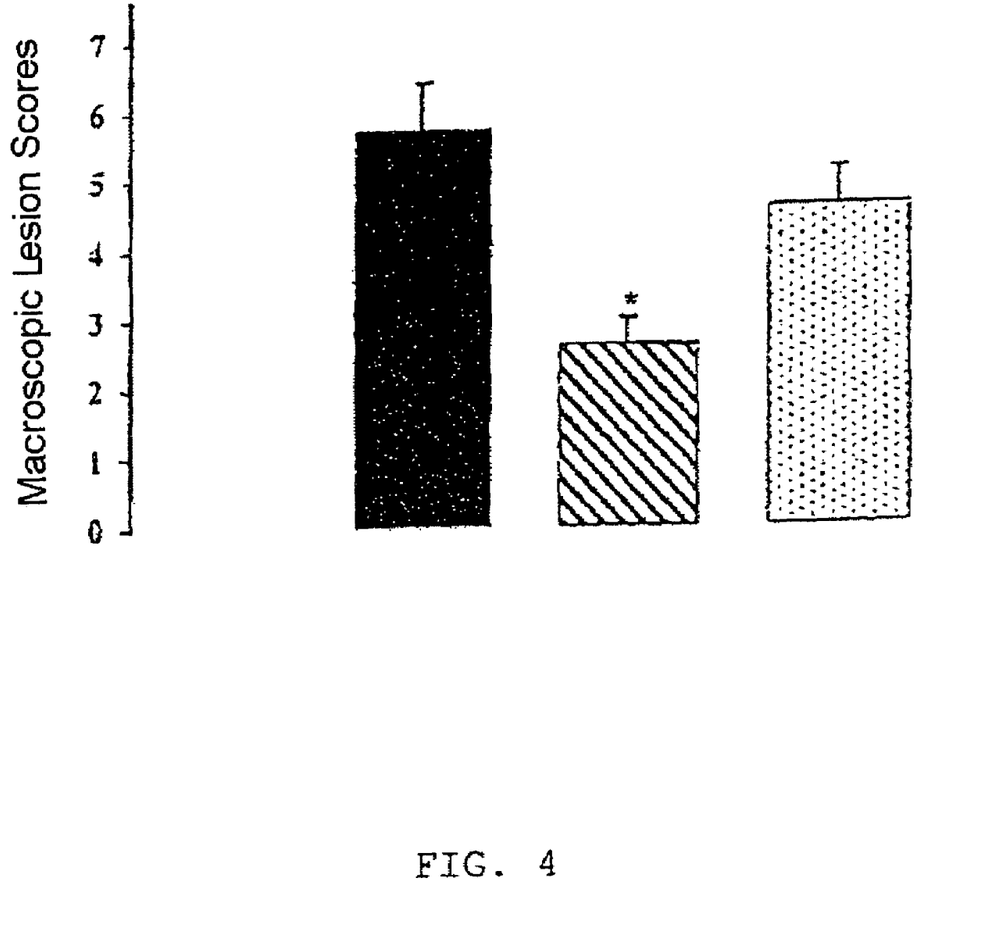
FIG. 4 shows macroscopic lesion scores in rats after treatment with *L. farciminis*.

The results are illustrated by FIG. 4.
Legend to FIG. 4:
On the x-axis
■=rats treated with TNBS/ethanol (group 3)
☒=rats treated with *L. farciminis*+TNBS/ethanol (group 4)
▨=rats treated with *L. farciminis*+TNBS/ethanol+Hb (group 5)
On the y-axis=macroscopic lesion score
*: significantly different (P<0.01) from the control group (groups 1 and 2)

Compared with the control rats considered as being free of macroscopic lesions (groups 1 and 2), TNBS/ethanol induces a colonic inflammation characterized by macroscopic lesions (group 3; 5.7±0.7). In the rats instilled with TNBS/ethanol, the treatment with *L. farciminis* very significantly reduces the lesion score (group 4; 2.6±0.4). This effect no longer appears when the treatment with *L. farciminis* is accompanied by an intracolonic infusion of Hb (group 5; 4.6±0.5).

III—Conclusion

The oral administration of *L. farciminis* reduces, in a similar manner to a treatment with SNP, the myeloperoxidase activity and the lesion score in rats treated with TNBS/ethanol.

These anti-inflammatory effects are abolished by the administration of an intracolonic infusion of hemoglobin, which shows that they call into play the production of NO.

EXAMPLE 2

Curative Effect of *Lactobacillus Farciminis* on a Colonic Inflammation Caused by TNBS/Ethanol The effects of a curative treatment with *L. farciminis* starting from the moment of induction of a colonic inflammation by TNBS/ethanol were studied.

4 groups of 10 male WISTAR rats of 200-250 grams are equipped, under anesthetic, with an intracolonic catheter as described in Example 1.

At D+5, the rats receive an instillation by the intracolonic route of 80 mg/kg of TNBS/ethanol (groups 1 and 2) or of a 0.9% NaCl solution (groups 3 and 4).

The treatment with *L. farciminis* starts 4 hours after the induction of inflammation. The rats receive by the oral route $10^{12}$ CFU/day of *Lactobacillus farciminis* (groups 1 and 3) or a 0.9% NaCl solution (groups 2 and 4), for 4 days.

At D+4, the rats are sacrificed and the severity of the inflammation of the colon wall is characterized by the myeloperoxidase (MPO) activity, on isolated colonic samples, as described in Example 1. The results are presented in FIG. 5.

Figure 5:
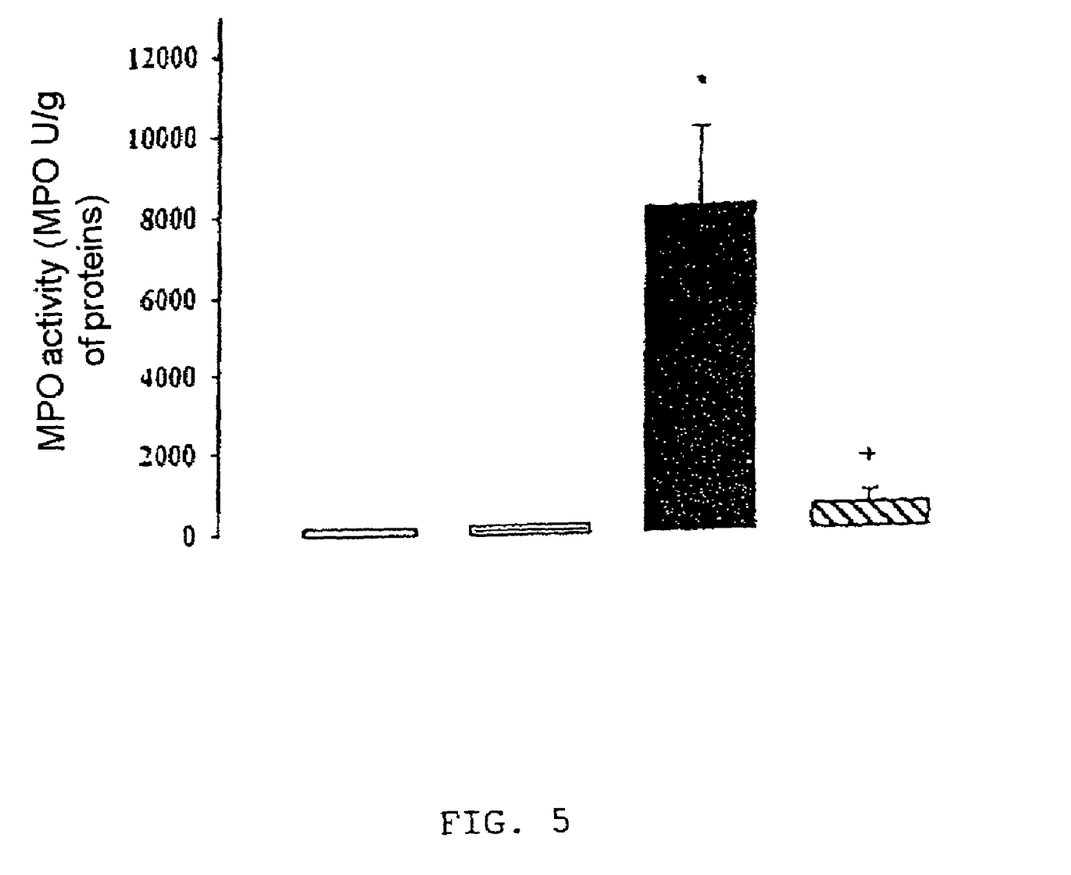
FIG. 5 shows the curative effect of *L. farciminis* on colonic inflammation.

Legend to FIG. 5:
On the x-axis
☐=untreated rats (group 4)
▨=rats treated with *L. farciminis* (group 3)
■=rats treated with TNBS/ethanol (group 2)
☒=rats treated with *L. farciminis*+TNBS/ethanol (group 1)

On the y-axis=MPO activity (MPO U/g of proteins)
*: significantly different (P<0.01) from the control group (group 4)
+: significantly different (P<0.01) from the TNBS/ethanol group (group 2)

The myeloperoxidase activity is greatly increased in the rats treated with TNBS/ethanol (group 2; 8184±1946 MPO U/g of proteins) compared with the untreated control rats (group 4; 76±16 MPO U/g of proteins). The treatment with *L. farciminis* does not increase the MPO activity in the rats instilled with the salt solution (group 3; 128±48 MPO U/g of proteins). By contrast, the treatment with *L. farciminis* of rats instilled with TNBS/ethanol (group 1; 584±299 MPO U/g of proteins) very significantly reduces the myeloperoxidase activity.

EXAMPLE 3

Effect of a Treatment with *Lactobacillus Farciminis* on Pain During Colorectal Destension The effects of a treatment with *L. farciminis* for visceral pain induced by colorectal distension were studied. This study was carried out in healthy rats (basal conditions) or under conditions of hyperalgesia induced by a colonic inflammation (inflammatory conditions) or a constraint stress (stress conditions). The pain during distension manifests itself by the increase in the number of contractions of the abdominal muscles (MORTEAU et al., Dig. Dis. Sci., 39, 1239-1248, 1994).

For 21 days, 7 groups of 10 male WISTAR rats of 200-250 grams receive by the oral route $10^{12}$ CFU/day of *Lactobacillus farciminis* (groups 2, 4 and 7) or a 0.9% NaCl solution (groups 1, 3, 5 and 6).

At D+7, the rats are equipped, under anesthetic, with an intracolonic catheter (+2 cm from the caecocolonic junction) and 3 groups of 3 NiCr electrodes are implanted on each side of the abdominal external oblique muscle just above the inguinal ligament. The catheter and the electrodes are accessible from the outside in the dorsoscapular region and protected by a glass tube attached to the skin.

I—Effect of a Treatment with *L. farciminis* Under Basal Conditions

At D+15, a colorectal distension is produced with the aid of a balloon inserted by the rectal route, 5 cm from the anus and attached to the animal's tail. The balloon is gradually inflated from 0 to 60 mmHg, in steps of 15 mmHg, each step lasting for 5 minutes. The abdominal muscle contractions are recorded with an electroencephalograph in order to visualize the visceral sensitivity. The results are illustrated by FIG. 6.

Figure 6:
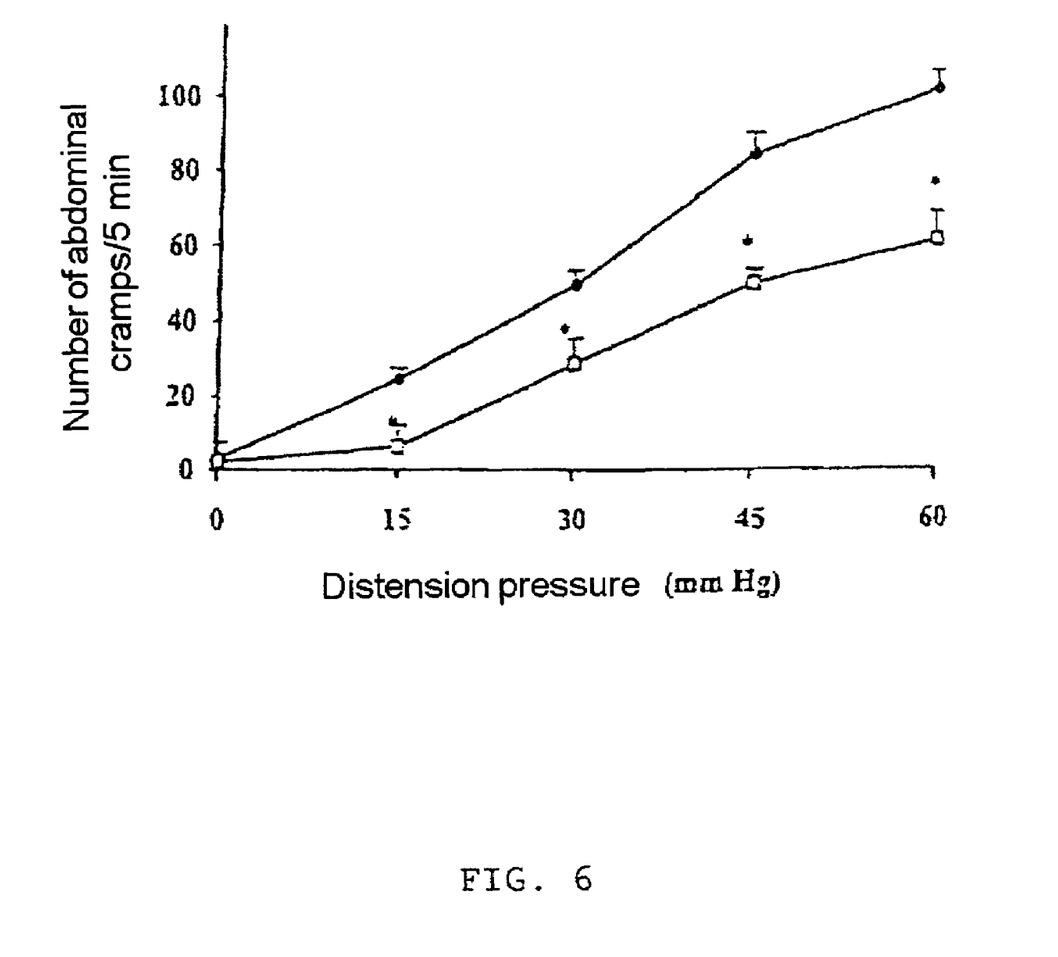
FIG. 6 shows the effect of treatment with *L. farciminis* under basal conditions, on pain during colorectal distension.

Legend to FIG. 6:
On the x-axis=distension pressure (mmHg)
On the y-axis=number of abdominal cramps/5 min
*: significantly different (P<0.05) from the control group (group 1)
Groups of Rats used:
♦=untreated rats (group 1)
□=rats treated with *L. farciminis* (group 2)

The progressive colorectal distension increases the number of abdominal muscle contractions according to the distension volume, whether the rats were treated with *L. farciminis* (group 2) or not (group 1). However, regardless of the distension volume, the number of abdominal muscle contractions is reduced in the rats treated with *L. farciminis* (group 2) compared with the untreated rats (group 1).

II—Effect of a Treatment with *L. farciminis* Under Inflammatory Conditions

At D+17, the rats receive the intracolonic instillation of 80 mg/kg of TNBS/ethanol (groups 3 and 4) or a 0.9% NaCl solution (group 1).

At D+21, that is 4 days after the intracolonic installation, a new session of colorectal distensions is performed as described above. The abdominal muscle contractions are recorded with an electroencephalograph in order to visualize the visceral sensitivity. The results are illustrated by FIG. 7.

Figure 7:
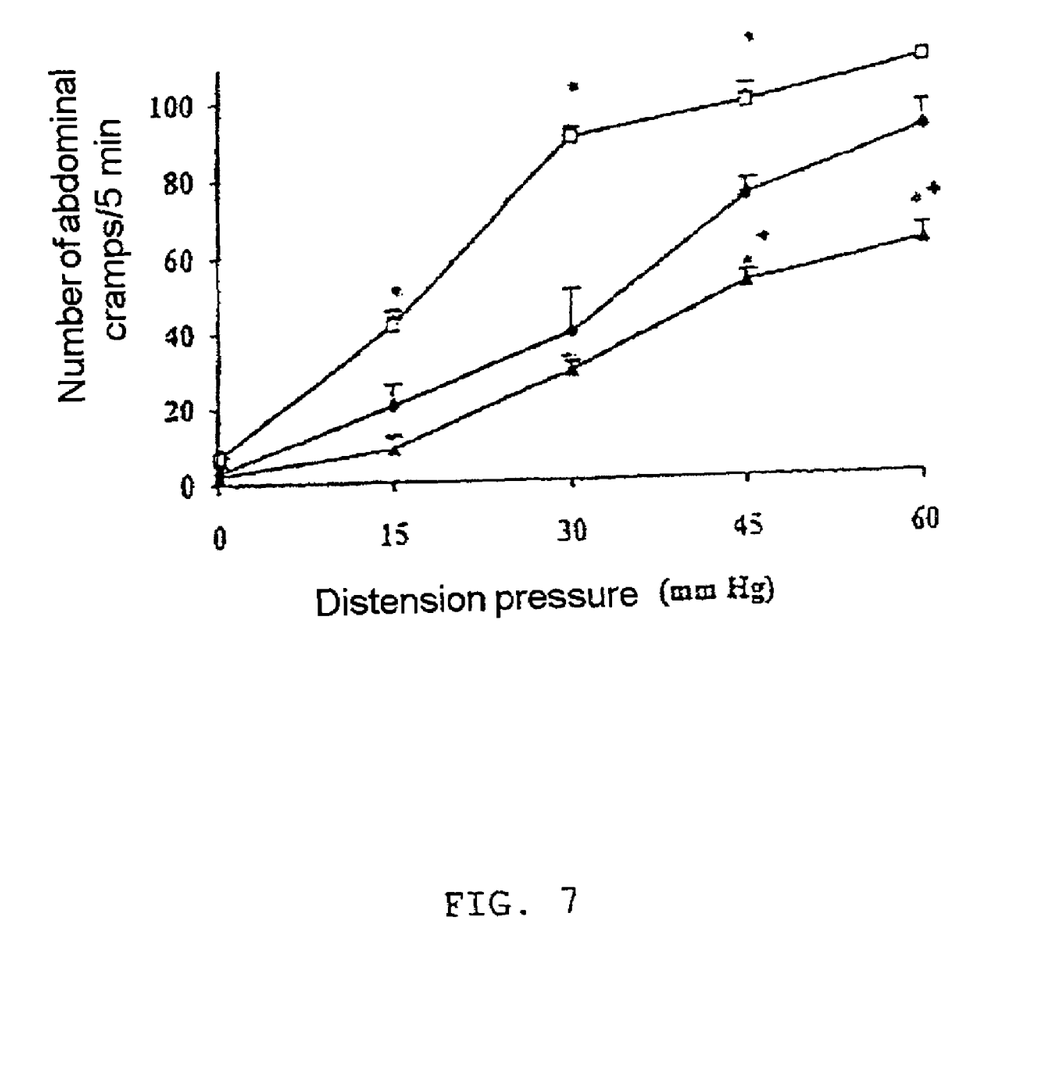
FIG. 7 shows the effect of treatment with *L. farciminis* under inflammatory conditions, on pain during colorectal distention.

Legend to FIG. 7:
On the x-axis=distension pressure (mmHg)
On the y-axis=number of abdominal cramps/5 min
*: significantly different (P<0.05) from the control group (groups 1 and 3)
Groups of Rats used:
♦=untreated rats (group 1)
□=rats treated with TNBS/ethanol (group 3)
▲=rats treated with *L. farciminis*+TNBS/ethanol (group 4)

The number of abdominal muscle contractions increases significantly 4 days after the instillation of TNBS/ethanol in the rats not treated with *L. farciminis* (group 3) compared with the control rats (group 1). The number of abdominal muscle contractions is significantly reduced 4 days after the instillation of TNBS/ethanol in the rats treated with *L. farciminis* (group 4) compared with the rats which received TNBS/ethanol but were not treated with *L. farciminis* (group 3) and is not significantly different from that of the control rats (group 1).

III—Effect of a Treatment with *L. farciminis* Under Stress Conditions

At D+15, the rats are subjected to a constraint stress (groups 6 and 7). Under a mild anesthetic with ether, the thorax and the forelimbs of the rats are surrounded with an adhesive tape so as to limit their movement. They are kept in this position for 2 hours. The control animals were only subjected to the ether anesthetic (group 5).

Twenty minutes after the constraint stress, a session of colorectal distensions is performed as described above. The abdominal muscle contractions are recorded with an electroencaphalograph in order to visualize the visceral sensitivity. The results are illustrated by FIG. 8.

Figure 8:
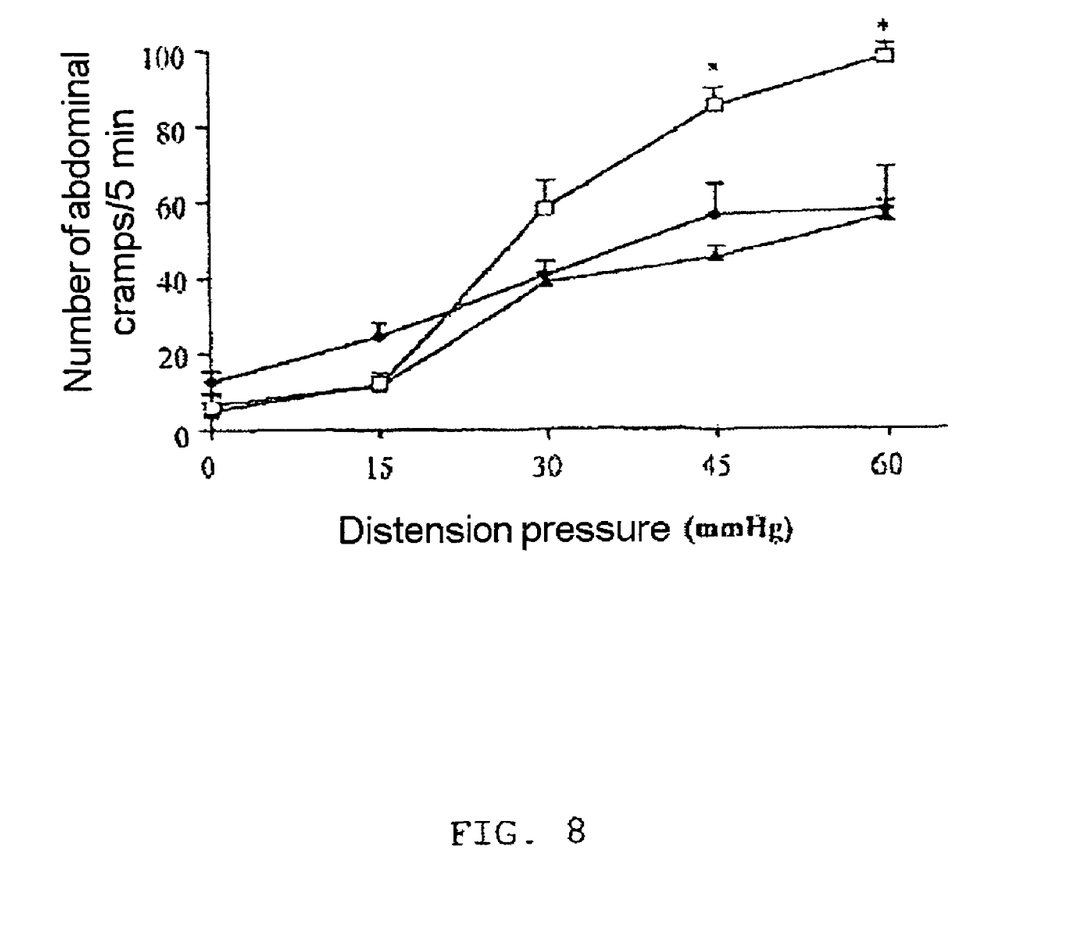
FIG. 8 shows the effect of treatment with *L. farciminis* under stress conditions, on pain during colorectal distension.

Legend to FIG. 8:
On the x-axis=distension pressure (mmHg)
On the y-axis=number of abdominal cramps/5 min
*: significantly different (P<0.05) from the control group (group 5)
Groups of Rats used
♦=untreated and unstressed control rats (group 5)
□=untreated and stressed rats (group 6)
▲=rats treated with L. farciminis and stressed (group 7)

The number of abdominal contractions corresponding to colorectal distensions of 45 to 60 mmHg is significantly increased after stress in the rats not treated with *L. farciminis* (group 6) compared with the control rats (group 5). For the 45 and 60 mmHg pressures, the number of abdominal contractions in the rats treated with *L. farciminis* and stressed (group 7) is significantly reduced compared with the untreated and stressed animals (group 6) and is not significantly different from that of the untreated and unstressed control animals (group 5).

IV—Conclusion

These results show that a treatment with *L. farciminis*, under basal conditions or conditions of hyperalgesia induced by a colonic inflammation or a constraint stress, reduces the number of abdominal muscle contractions, indicating a reduction in visceral pain.

The invention claimed is:

1. A method of treating colitis comprising administering to a patient in need thereof an effective amount of a composition comprising lactic acid bacteria *Lactobacillus farciminis*.

2. The method of claim 1 wherein said colitis results from a pathology selected from the groups consisting of Crohn's disease, hemorrhagic rectocolitis, and irritable bowel syndrome.

3. The method of claim 1 wherein the composition is in the form of a foodstuff or a dietary supplement.

* * * * *